United States Patent [19]

Kohli

[11] Patent Number: 5,026,872

[45] Date of Patent: Jun. 25, 1991

[54] AROMATIC ETHER-KETONE POLYAMINES, INTERMEDIATES AND PRODUCTS, AND METHODS FOR PREPARING SAME

[75] Inventor: Dalip K. Kohli, Norwalk, Conn.

[73] Assignee: American Cyanamid, Me.

[21] Appl. No.: 576,231

[22] Filed: Feb. 1, 1984

[51] Int. Cl.$^5$ ............... C07D 207/452; C07C 211/00; C07C 213/00; C07C 221/00

[52] U.S. Cl. .................................. 548/521; 564/328; 564/336; 564/346; 564/347

[58] Field of Search ............... 548/521; 564/328, 336, 564/346, 347

[56] References Cited

U.S. PATENT DOCUMENTS

| | | | |
|---|---|---|---|
| 3,932,368 | 1/1976 | Cerankowski et al. | 528/64 |
| 4,316,844 | 2/1982 | Waitkus et al. | 528/185 |
| 4,517,321 | 5/1985 | Gardner et al. | 523/445 |

OTHER PUBLICATIONS

Chem. Abstracts 91:158766t Thermosetting Resin Laminate.

*Primary Examiner*—John Kight, III
*Assistant Examiner*—P. Hampton-Hightower
*Attorney, Agent, or Firm*—Steven Flynn

[57] ABSTRACT

Novel aromatic ether ketone diamine compounds and methods for their preparation are disclosed which comprise from about 3 to 8 aromatic rings interspersed with ether and ketone linkages. The novel ether ketone diamine compounds are useful as monomeric starting materials for the preparation of useful intermediates and useful thermoplastic and high temperature resistant polymers. In preferred embodiments, the novel ether ketone diamines are useful as curing agents for epoxy resin compositions and composite materials.

8 Claims, 1 Drawing

AROMATIC ETHER-KETONE POLYAMINES, INTERMEDIATES AND PRODUCTS, AND METHODS FOR PREPARING SAME

BACKGROUND OF THE INVENTION

The present invention relates to novel aromatic ether ketone polyamine compounds useful as curatives for polyepoxide compositions and as monomeric starting materials for the preparation of useful intermediates and useful thermoplastic and highly heat resistant polymers. The present invention also relates to methods for preparing the polyamines, epoxy resin compositions, intermediates and polymeric materials.

Polyamines are known to react with a wide variety of reactive groups to form useful compounds and compositions. Amine groups react with isocyanate groups to form ureas useful as herbicides and fungicides as well as in coatings and film applications. Amines react with carboxylic acid groups to form amides useful as film and fiber formers as well as coatings and thermoplastic molding compositions. When reacted with carboxylic acid anhydrides, amines are useful for forming polyamides exhibiting high temperature resistance which are employed in heat shield and wire enamels applications. Polyamines also react with epoxide prepolymers to cure them by a polyaddition reaction to form tough, crosslinked resinous compositions having utility as encapsulants for electronic components, adhesives, coatings and the like.

When the epoxy resin compositions are filled and reinforced with, for example, glass or graphite fibers, reinforced epoxy resin composites are obtained having high strength to weight ratios. These reinforced composite materials have found extensive use in the aircraft and aerospace industries, and in other applications where strength, corrosion resistance and light weight are desirable. For instance, fiber resin matrix materials have replaced aluminum and other metals in primary and secondary structures of modern military and commerical aircraft. Sporting equipment such as tennis rackets and golf clubs have also adopted fiber resin materials successfully.

Epoxy resin compositions and fiber modifications are abundant. Since the advent of fiber resin matrix materials, much effort has been expended in improving their properties and characteristics, including the development of many different curing systems.

Amine and polyamine curing agents have received wide acceptance, but the toxicity, low solubility, high exotherm and variable curing rates associated with the most commonly used amines, such as m-phenylenediamine, 4,4'-diaminodiphenyl methane and 4,4'-diaminodiphenyl sulfone, has made further improvement desirable. In the case of aircraft structural applications, epoxy resins cured with available curing agents are either too brittle or do not have sufficient strength and stiffness under hot/wet conditions. It is disclosed in U.K. Patent 1,182,377, which is incorporated herein by reference, that certain aromatic polyamines having the formula:

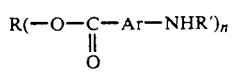

wherein R represents the radical formed after elimination of the hydroxyl group of a polyhydric aliphatic, cycloaliphatic or aralphatic alcohol, Ar represents an optionally substituted phenylene or naphthylene radical, R' represents hydrogen or an alkyl radical an n represents an integer from 2 to 10, are effective as curing agents for a variety of polyepoxides, and the resulting cured compositions are useful as films, moldings, coatings and glass-reinforced laminates. There is no indication in the properties presented in the U.K. Patent that the curing agents exemplified therein will produce the combination of toughness and strength under hot/wet conditions essential for use in the above-mentioned structural applications.

In U.S. Pat. No. 3,932,360, diamine cured polyurethane products are described, in which the diamines are of the formula, e.g.,

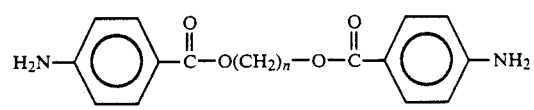

wherein n is an integer from 2 to 12. This '360 patent does not deal with curing compounds having more than one epoxide group per molecule.

In Gillham et al, Organic Coatings and Applied Polymer Science Proceedings, Vol. 46, p. 592–598, March-April, 1982, polyepoxides cured with diamines of the immediately preceding formula (n is 3), are described.

In Chemical Abstracts, 90:39660y, bis(aminophenoxy) compounds, such as 4,4'-bis(3-aminophenoxy)diphenylsulfone, are disclosed to be useful crosslinking agents for bisphenol-A- epichlorohydrin copolymer resins and provided improved heat distortion temperature and improved flexibility to that cured epoxy resin, as compared with a similar composition cured with a diaminodiphenylmethane crosslinking agent.

In Chemical Abstracts, 91:158766t, thermosetting resin laminates having good flexibility and machinability are disclosed which are, prepared by impregnating a glass textile with a thermocurable composition comprising an epoxy resin (ARALDITE® 8011, from Ciba-Geigy Corporation); a diamine of the formula:

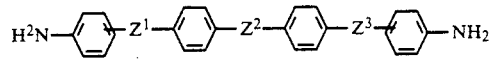

wherein $Z^1$, $Z^2$ and $Z^3$ are O, S, $SO_2$, $CH_2$, CO, $CO_2$ or $C(CH_3)_2$ and 2-ethyl-4-methylimidazole; processing the impregnated fabric at 160° C. to form a prepreg; laying up several layers of prepregs and fusing at 170° C. and 90 kg/cm² for 1½ hours.

In copending application, Ser. No. 584,700, filed Feb. 29, 1984, now U.S. Pat. No. 4,645,803, it is disclosed that neat resins comprising an epoxidic prepolymer having more than one epoxide group per molecule and a polyamine curing agent are provided with improved toughness and hot/wet modulus if the polyamine curing agent employed is an aromatic ether sulfone polyamine or aromatic ether ketone polyamine polyamine compound having the formula:

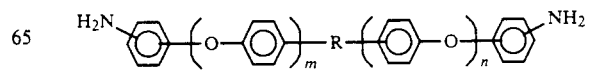

wherein R is selected from

m=n; and m and n are integers of from 1 to 5. Reinforced composites such as prepregs and laminates comprising these curable compositions as the resin component are disclosed to have improved compression strength and short beam shear strength under dry, hot and hot/wet conditions.

It has now been discovered that novel polyamine compounds having a backbone containing from about 3 to about 8 aromatic rings interspaced by ether and ketone groups are useful as monomeric reactants for forming polymeric materials exhibiting improved impact resistance, solvent resistance and moisture resistance, as compared with simpler aromatic polyamines, aromatic ether-sulfone polyamines or simple ether ketone polyamines. When the novel aromatic ether-ketone diamines of the present invention are used as curing agents for epoxy resin compositions both neat resins and reinforced epoxy resin composites are obtained which exhibit excellent retention of physical properties under hot/wet conditions.

SUMMARY OF THE INVENTION

It is an object of the present invention to provide novel aromatic ether-ketone polyamine compounds which are useful, for example, as comonomers for the formation of condensation polymers and as curing agents suitable for use with compounds having more than one epoxide group per molecule.

It is another object of the present invention to provide a method for the preparation of novel aromatic ether-ketone diamine compounds It is a further object of the present invention to provide new and useful reactive intermediates, such as bismaleimide compounds, for use in epoxy resin compositions.

In accordance with these and other objects, the present invention provides new and improved polyamine compounds having the formula:

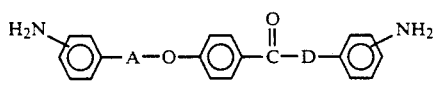

wherein A is a valence bond or a divalent radical selected from the group consisting of:

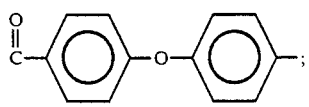

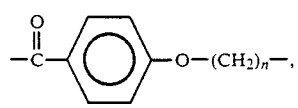

wherein n is an integer of from 1 to 10;

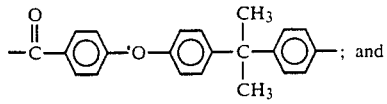

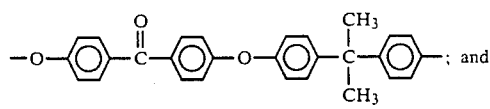

D is valence bond or a

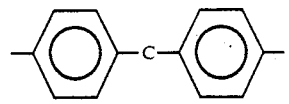

radical.

In accordance with the method of the present invention, the novel aromatic ether ketone diamine compounds may be prepared by:

(a) forming a reaction mixture comprising 3- or 4-amino-4'-chlorobenzophenone and
 (i) m- or p- aminophenol;
 (ii) a dihydric phenol compound; or
 (iii) mixtures of (i) and (ii), in an alkaline medium in a polar aprotic solvent; and (b) thereafter, reacting the reaction mixture (a) at a temperature of between 30° C. and 300° C. until the reaction is substantially complete.

In an alternate method, in accordance with the present invention, the aromatic ether ketone diamine compounds may be prepared by:

(a) forming a reaction mixture of
 (i) 3- or 4- amino-4'-chlorobenzophenone and
 (ii) a dialkali metal salt of a dihydric phenol or an alkali metal salt of m- or p- aminophenol, in a polar aprotic solvent; and (b) reacting the mixture of step (a) at a temperature of between 30° C. and 300° C. until the reaction is substantially complete.

In a preferred embodiment, the present invention provides a method for preparing a flexible aromatic ether ketone diamine compound, the method comprising:

(a) reacting a bis(aryloxy) alkane compound having the formula:

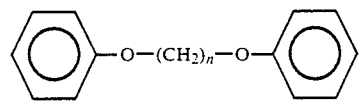

wherein n is an integer of from 1 to 10; with m- or p-nitrobenzoyl chloride in the presence of a Lewis acid catyalyst; and (b) thereafter, reducing the nitro group present in the reaction product of step (a) to amine groups by reactive hydrogenation.

The novel aromatic ether ketone diamine compounds of the present invention are useful as monomeric materials for the preparation of high molecular weight linear condensation polymers such as polyamides and polyimides. The novel aromatic ether-ketone diamine compounds are useful for forming reactive intermediates, such as bismaleimide compounds. Moreover, the novel aromatic ether ketone diamine compounds of the present invention are well-suited for use as curing agents for curable epoxy resin or urethane resin compositions.

More particularly, in accordance with an especially preferred embodiment of the present invention new and improved curable epoxy resin compositions are provided in the form of a composition comprising:

(a) reinforcing filaments; and (b) a heat-curable epoxy resin composition comprising:

(i) an epoxy prepolymer or combination of prepolymers having more than one epoxide group per molecule, and (ii) an amount effective to promote cure of said epoxy prepolymer of an amine-functional curing agent or combination of curing agents selected from those of the formula:

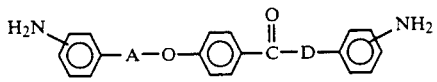

wherein A is a valence bond or a divalent radical selected from the group consisting of:

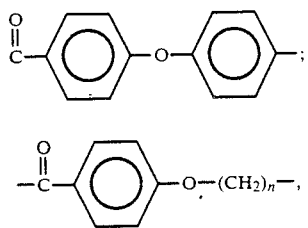

wherein n is an integer of from 1 to 10;

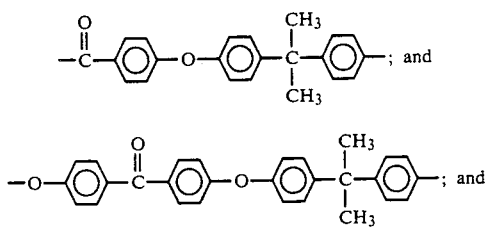

D is valence bond or a

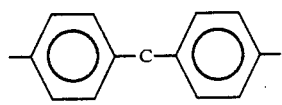

radical.

In another aspect of this embodiment, of the present invention contemplates fiber reinforced heat-curable epoxy resin compositions comprising:

(i) an epoxy prepolymer or combination of prepolymers having more than one epoxide group per molecule, and (ii) an amount effective to promote cure of of an amine-functional curing agent or combination of curing agents selected from the aromatic ether ketone diamine compounds of the present invention having the formula outline above.

It is among the preferred features of this aspect of the invention to provide such compositions in filled and/or reinforced, e.g., glass fiber reinforced embodiments, which are useful as prepregs, for example to make laminates and other structural shapes in accordance with procedures known in this art.

In another preferred aspect of this embodiment, the present invention provides compositions of epoxy resins and the above-mentioned diamine curing agents which also include a second resin in amount sufficient to impart improvements in mechanical properties, especially toughness, while preserving substantial resistance to failure under hot/wet conditions. Such resins can be present homogeneously and also in the form known as interpenetrating polymer networks. Particularly useful in this aspect are resins which include repeating units of the formula:

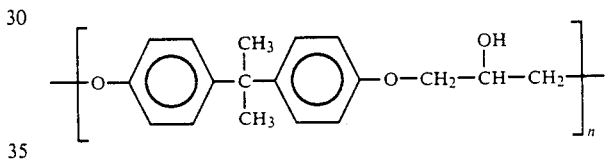

and those with repeating units of the formula:

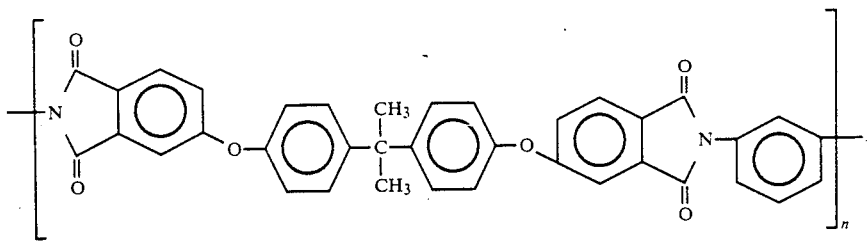

wherein n is a number sufficient to provide a molecular weight of 20,000 to 60,000. Amounts of 5 to 30, preferably 10 to 20 parts by weight per 100 parts by weight of epoxy prepolymer can be used.

Generally, and without limitation aromatic ether-ketone polyamine curing agent or agents are employed in an amount of from about 25 to 95 parts by weight, based upon 100 parts by weight of the epoxidic prepolymer or prepolymer mixture. The curable resin compositions of the present invention may generally be prepared by admixing the epoxy prepolymer and the curing agent at from about 70° to about 125° C. until thorough mixing is achieved. The neat resin mixture may thereafter be used to impregnate fabrics and fibers to form prepregs. Both the neat resin compositions and the prepregs may be thermally cured by heating to temperatures of from about 135° to about 180° C.

The new and improved neat resins of the present invention exhibit improved toughness and hot/wet modulus properties, and prepregs and laminates prepared therewith exhibit significant improvements in composite properties such as compression stength and short beam shear strength.

Other objects and advantages of the present invention will become apparent from the following detailed description of the invention and illustrative working Examples, taken in conjunction with the formal drawings in which:

DETAILED DESCRIPTION OF THE INVENTION

Figure 1:
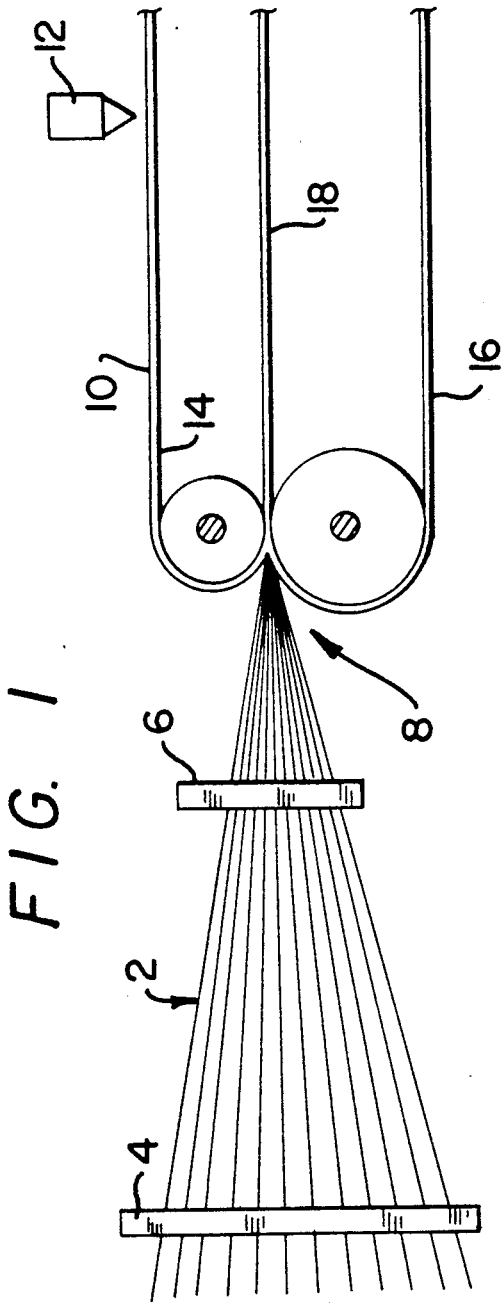
FIG. 1 is a schematic of one method for preparing a fiber resin matrix prepreg tape of the present invention.

In accordance with the present invention, novel and useful aromatic ether ketone diamine compounds are provided, which are generally represented by the formula:

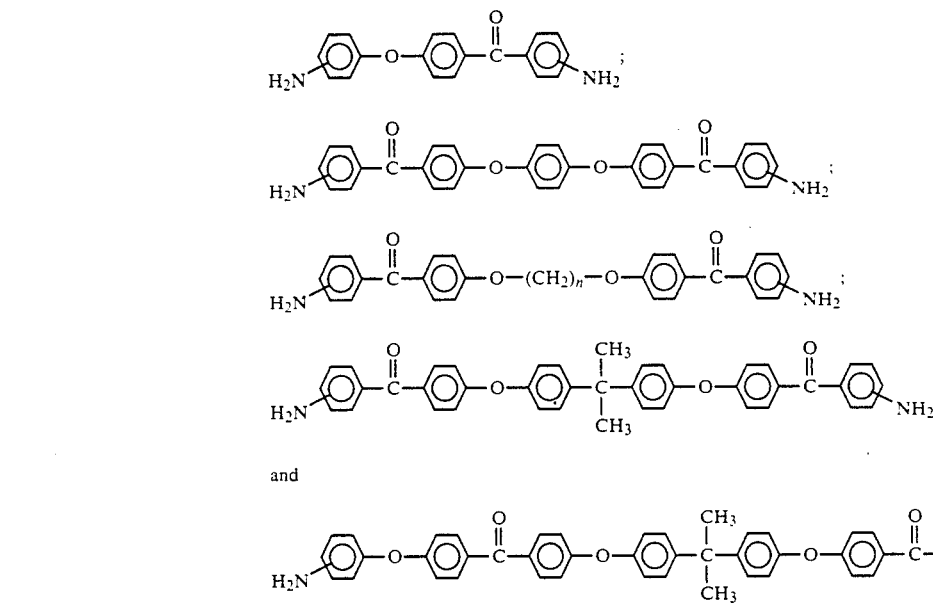

wherein A is a valence bond or a divalent radical selected from the group consisting of:

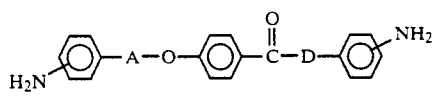

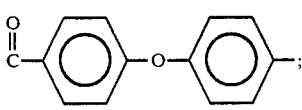

wherein n is an integer of from 1 to 10;

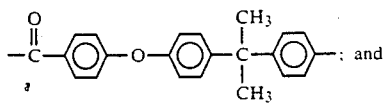

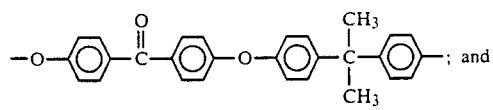

D is valence bond or a

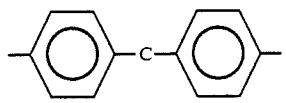

radical.

The preferred aromatic ketone diamine compounds within the above formula are:

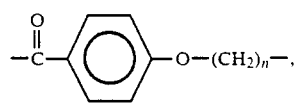

The novel ether ketone diamine compounds of the present invention may be prepared in accordance with the methods of the present invention, more fully described hereinafter.

In accordance with one method of the present invention, the ether ketone diamines are synthesized by reacting 3- or 4-amino-4'-chlorobenzophenone with a dihydric alcohol in an alkaline medium in a polar aprotic solvent at a temperature between about 30° C. and 300° C. for for a time sufficient to permit the reaction to proceed substantially to completion.

More particularly, the 3- or 4- amino-4'-chlorobenzophenone starting materials may be prepared by first reacting 3- or 4- nitrobenzoyl chloride with chlorobenzene by a Friedel-Crafts reaction in the presence of a Lewis acid catalyst, for example boron trifluoride, BF₃, aluminum chloride, AlCl₃, or stannic chloride SnCl₄. The 3- or 4-nitro-4'-chlorobenzophenone product may thereafter be reduced to form the 3- or 4-amino-4'-chlorobenzophenone starting material by a reductive hydrogenation reaction, for example by reducing with HCl in the presence of a metal such as stannous chloride, or reducing with hydrogen gas in the presence of a nickel or platinum or palladium catalyst, or by reaction with metal hydrides and other known methods. The reactions may be summarized as follows:

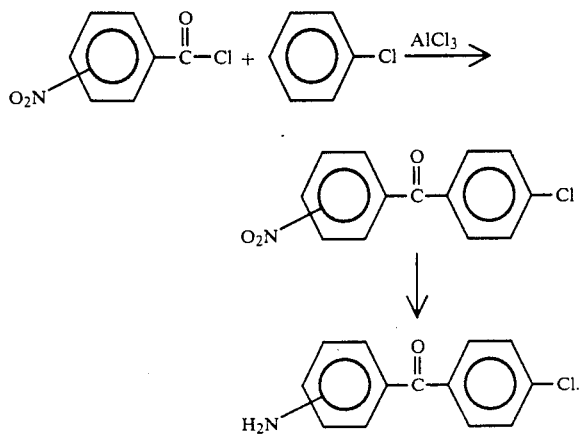

The novel ether ketone diamine compounds may thereafter be prepared by reacting the 3- or 4-amino-4'-chlorobenzophenone with an m- or p-aminophenol with a dihydric alcohol in an alkaline medium in a polar aprotic solvent with heating to temperatures of between about 30° C. and 300° C. Suitable alkaline components may be selected from hydroxides of alkali metals, such as sodium, lithium and potassium and alkaline earth metals such as barium, calcium and strontium. Suitable polar aprotic solvents are, for example, dimethylsulfoxide, dimethylformamide, tetrahydrofuran and dimethylacetimide, to name but a few.

Alternatively, the ether ketone diamines may be prepared by reacting 3- or 4-amino-4'-chlorobenophenone with the alkali metal salt of m- or p- aminophenol or the dialkali metal salt of the dihydric alcohol in the presence of a polar aprotic solvent. These syntheses may be summarized by employing preferred materials as follows:

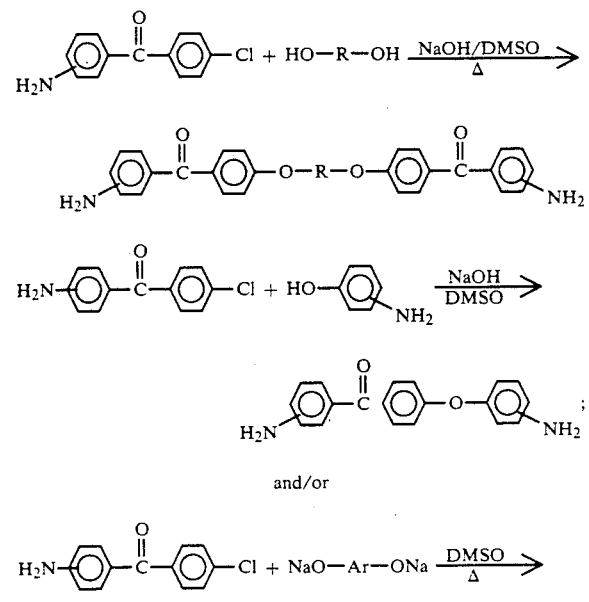

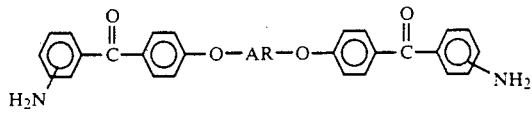

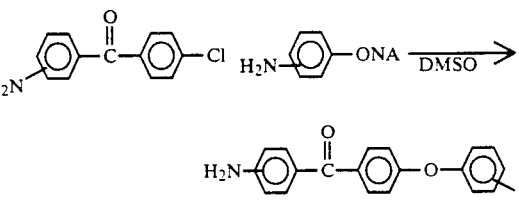

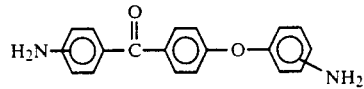

Generally, and without limitations, good yields of the above-descibed aromatic ether ketone diamines will be obtained in accordance with the methods of the present invention, if approximately equal molar proportions of 3- or 4-amino-4'-chlorobenzophenone and the dihydric phenol, aminophenol or alkali metal alcoholate derivatives are employed. The amount of alkali metal or alkaline earth metal hydroxide employed is also not critical to the process, provided the reaction medium is alkaline.

In an especially preferred embodiment, the present invention provides a method for preparing flexible aromatic ether-ketone diamines having the formula:

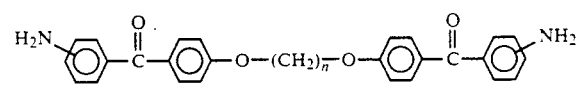

The method comprises the steps of:

(a) reacting a bis aryloxy alkane compound compound having the formula:

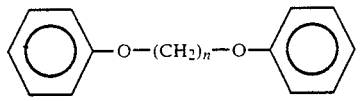

wherein n is an integer of from 1 to 10; with m- or p-nitrobenzoyl chloride in presence of a Lewis acid catalyst; and (b) thereafter subject the nitro compound formed in step (a) to reductive hydrogenation conditions to reduce the nitro groups to amine groups.

Illustrative bis aryloxyalkane compounds which may be employed in the process are for example, bisphenoxymethane, bisphenoxy ethane, 1,3-bisphenoxypropane, 1,4-bisphenoxybutane, 1,5-bisphenoxypentane and the like. Suitable Lewis acid catalysts for use in this method are boron trifluoride, aluminum chloride and stannic chloride, which are employed in their conventional amounts.

The reductive hydrogenation conditions herein are the same as those referred to above, e.g., HCl and $SnCl_2$ or $H_2$ and Pt.

In a preferred aspect, the aromatic etherketone diamine compounds of the present invention are suitable for use as curing agents for epoxy resin compositions. In accordance with this aspect of the invention, new and improved heat curable epoxy resin compositions are provided which exhibit exceptionally high modulus properties under dry, wet and hot/wet conditions.

In general, the new and improved epoxy resin compositions of the present invention are prepared by mixing the polyepoxide compounds with the polyamines of the above-mentioned formula in an amount sufficient to provide an equivalent ratio of epoxy groups to amine groups of from about 1:1 to about 10:1, preferably from about 2:1 to about 8:1 and especially preferably from about 3:1 to about 5:1. The admixture is optionally heated, for example to a temperature of between about 30° C. and 300° C. and preferably to a temperature of about 70° C. to about 125° C., until a melt is obtained. The melt can then be poured into a mold and reacted, for example, for two hours at approximately 135° C. and then for three hours at approximately 180° C., to form moldings showing outstanding mechanical and electrical properties.

Fillers, pigments, dyes, reinforcements, such as glass fibers or woven cloths, plasticizers, and mixtures thereof, may be added to the epoxy resin-polyamine composition before the reaction in order to modify ultimate properties, in known ways. Applications can also be made by trowelling, brush coating, immersion or dip coating, spraying and other conventional methods. Catalysts, such as boron trifluoride - organic amine adducts, and the reaction product of toluene 2,4-diisocyanate and dimethylamine can also be included, in quantities of from e.g., 0.1 to 5% by weight based on the resin-polyamine, to accelerate curing.

The fiber resin matrix compositions according to the present invention can be prepared by embedding filaments, e.g., glass fibers and/or non-siliceous filaments in a curable resin composition to form a fiber resin matrix which can be manipulated and cured to a solid composite. Particular selection of the filament material, epoxy prepolymer and curing agent, as well as including optional ingredients such as fillers, dyes, catalysts, processing aids, etc., can give a range of curable compositions heretofore unknown in the art and exhibiting improved physical properties over known materials.

Glass filaments useful herein are well known. The non-siliceous filament component may be of any non-glass, non-silicon dioxide-containing material which improves the strength or other physical properties of the curable epoxy resin component (described infra.) Such filaments include, but are not limited to, filaments comprised of carbon, graphite, silicon carbide, boron, aramid, polyester, polyamide, rayon, polybenzimidazole, polybenzothiazole, metal-coated such filaments, for example, nickel-coated and/or silver-coated graphite fibers and filaments, or combinations of such filaments. Fibers (woven or non-woven), tows or mats of such filaments, or tapes (unwoven, flat bundles of the unidirectional filaments) may be employed as desired. In applications demanding high stiffness-to-weight ratio or shear strength, carbon fibers, graphite filaments, polyaramid filaments or nickel-plated graphite filaments, as disclosed in assignee's copending application Ser. No. 358,637 filed Mar. 16, 1982 now abandoned, are most preferred.

The epoxy resins suitable for use in the present invention are compounds having more than one epoxide group per molecule available for reaction with the primary polyamine curing agents of the present invention. Such epoxy prepolymers include but are not limited to polyglycidyl ethers of polyvalent phenols, for example pyrocatechol; resorcinol, hydroquinone; 4,4'-dihydroxydiphenyl methane; 4,4'-dihydroxy-3,3'-dimethyldiphenyl methane; 4,4'-dihydroxydiphenyl dimethyl methane; 4,4'-dihydroxydiphenyl methyl methane, 4,4'-dihydroxydiphenyl cyclohexane; 4,4'-dihydroxy-3,3'-dimethyldiphenyl propane; 4,4'-dihydroxydiphenyl sulfone; or tris-(4-hydroxyphenyl)methane; polyglycidyl ethers of the chlorination and bromination products of the above-mentioned diphenols; polyglycidyl ethers of novolacs (i.e., reaction products of monohydric or polyhydric phenols with aldehydes, formaldehyde in particular, in the presence of acid catalysts); polyglycidyl ethers of diphenols obtained by esterifying 2 mols of the sodium salt of an aromatic hydrocarboxylic acid with 1 mol. of a dihaloalkane or dihalogen dialkyl ether (U.K. 1,017,612); and polyglycidyl ethers of polyphenols obtained by condensing phenols and long-chain halogen paraffins containing at least two halogen atoms (U.K. 1,024,288).

Other suitable compounds include polyepoxy compounds based on aromatic amines and epichlorohydrin, for example N, N'-diglycidyl-aniline; N,N'-dimethyl-N,N'-diglycidyl -4,4'-diaminodiphenyl methane; N,N,N',N'- tetraglycidyl-4,4'-diaminodiphenyl methane; and N-diglycidyl-4-aminophenyl glycidyl ether. Special mention is made of N,N, N',N'-tetraglycidyl-1,3-propylene bis-4-aminobenzoate.

Glycidyl esters and/or epoxycyclohexyl esters of aromatic, aliphatic and cycloaliphatic polycarboxylic acids, for example phthalic acid diglycidyl esters and adipic diglycidyl ester and glycidyl esters of reaction product of 1 mol of an aromatic or cycloaliphatic dicarboxylic acid anhydride and ½ mole of diol or 1/n mol of a polyol with n hydroxyl groups, or hexahydrophthalic acid diglycidyl, optionally substituted by methyl groups, are also suitable.

Glycidyl ethers of polyhydric alcohols, for example of 1,4-butanediol; 1,4-butenediol; glycerol; 1,1,1-trimethylol propane; pentaerythritol and polyethylene glycols may also be used. Triglycidyl isocyanurate; and polyglycidyl thioethers of polyvalent thiols, for example of bis mercaptomethylbenzene; and diglycidyltrimethylene sulfone, are also suitable.

Preferably the epoxy prepolymer component will be selected from compounds having the idealized formula:

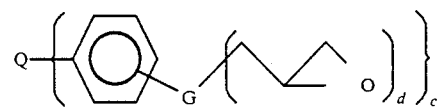

and halogen and alkyl substituted derivatives of such compounds, wherein c is 2, 3 or 4 and equal to the valence of Q; Q is a divalent, trivalent or tetravalent radical; G is —O—, NR'— or

R is hydrogen or alkyl; and d is 1 or 2 depending on the valence of G.

The most preferred epoxy compound will include the following:

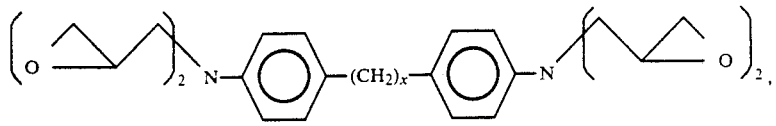

wherein x is an integer from 1 to 4, available commercially (where x=1) as ARALDITE® MY-720 (Ciba-Geigy);

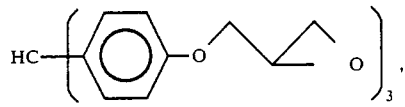

available commercially as XD 7342 (Dow Chemical);

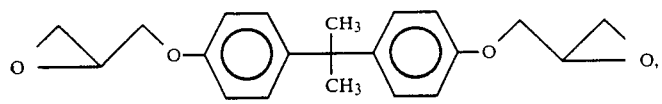

available commercially as DER 331 (Dow Chemical) or Epon® 828 (Shell);

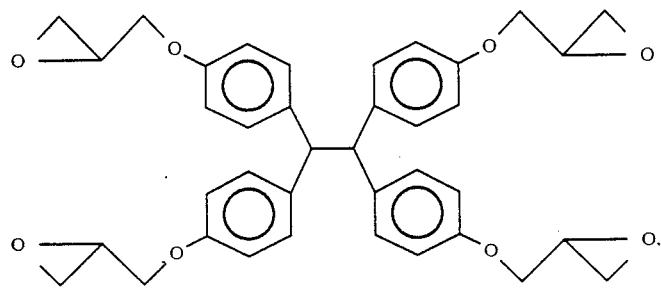

available commercially as EPON® 1031 (Shell);

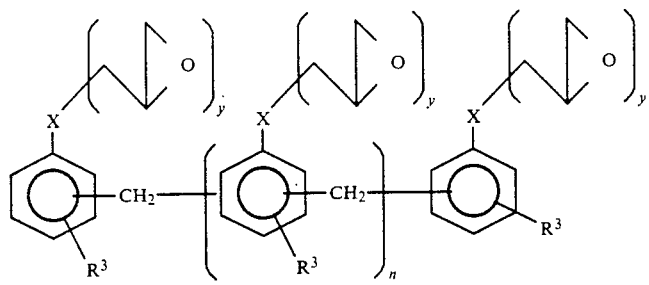

wherein Y is 1 or 2, X is —O— or —NH, $R_3$ is H or $CH_3$ and n is 2 to 8.

Compound in which X is —O— are available as a mixture under the tradename DEN-438 from Dow Chemical Company.

Also preferred are triglycidyl ethers of meta- and para-hydroxyaniline, e.g., represented by the formula:

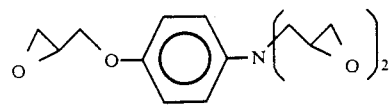

These are available under the tradename ARALDITE® 0500, 0510 from Ciba-Geigy.

In accordance with this aspect of the present invention, the epoxide prepolymers or mixtures of prepolymers are cured with the novel aromatic ether ketone polyamine compounds identified and described above, to provide thermocurable epoxy resin compositions exhibiting improved strength and toughness and improved hot/wet modulus properties over prior art compositions.

The new and improved epoxy resin compositions of the present invention may be used as neat resins, alone or in admixture with reinforcing fibers, fillers, pigments, dyes, curing catalysts and other conventional additives and processing agents. Also contemplated are the use of the above-described curing compounds in combination with other conventional polyamines such as methylene dianiline, phenylene diamine, and the like.

In an alternate aspect, the new and improved epoxy resin compositions are employed to form fiber-matrix compositions.

More particularly, one method of forming the fiber matrix composition of the present invention is illustrated in the drawings. As seen in FIG. 1, the basic fiber matrix material is produced by delivering fiber 2 through conventional eyeboards 4 and 6 to a pressure roller assembly 8. The resin composition is coated in a layer 10 from a conventional film coating application 12 onto a substrate such as release paper 14 and passed through the pressure roller assembly 8. Release paper 16 is also delivered to the pressure roller assembly 8.

The pressure rollers 8 are set at a temperature and pressure for imbedding the fibers 2 in the resin layer 10 to form a fiber matrix composition 18. Practice has taught that a temperature in the range of 190° F. and pressures of one thousand pounds over fifteen inch centers are suitable for producing fiber resin prepreg tape 18.

The fibers 2, the substrate 14 with resin layer 10 and the release paper 16 are delivered to the pressure rollers 8 and passed therethrough at the rate of 5-20 feet/minute.

Figure 2:
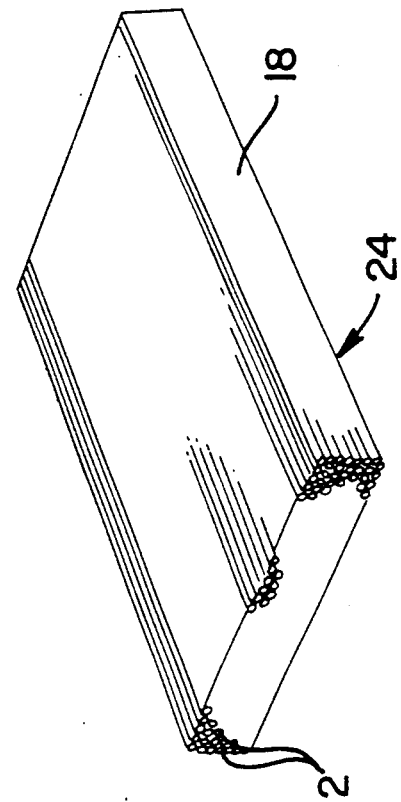
FIG. 2 is an enlarged cross-sectional view of a strip of the fiber resin matrix prepreg tape of the invention.

The feed of fiber 2 and resin layer 10 to the pressure rollers 8 is selected to produce a fiber matrix of about twenty to sixty weight percent resin and about eighty to forty weight percent fiber. For example, one hundred twenty spools of 6K carbon fibers are delivered within a twelve inch width to the pressure rollers 8 with a layer of resin 0.009 to 0.0013 pounds per square foot. The resulting fiber resin matrix 18 results in a generally parallel array of fibers, shown by FIG. 2.

Fillers, pigments, dyes, curing catalysts and other such conventional additives and processing aids may be added to the fiber matrix compositions of the invention before curing to influence the properties of the final resin composite. In addition, polymeric additives such as the butadiene-styrene-acrylonitrile core-shell polymers and the like can be included for their known effects on polymer properties.

The new and improved epoxy resin compositions of the present invention provide thermally curable neat resin compositions which exhibit an increase in flexural failure strength and strain, and improved toughness and improved hot/wet modulus. The epoxy resin compositions of the present invention are useful in fiber resin matrix compositions to provide advanced composite materials exhibiting improved compression strength and improved toughness under dry, wet or hot/wet conditions. The compositions of the present invention are well suited for use as improved primary structures in aircraft and other structural applications, as well as adhesives and in electrical uses, such as potting compounds and printed circuit board substrates.

In accordance with an alternate aspect of this invention, the novel aromatic ether ketone diamines of the invention defined above are useful for forming novel reactive intermediates, such as bis maleimide compounds having the formula:

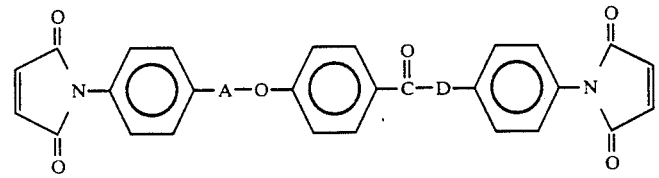

wherein A is a valence bond or a divalent radical selected from the group consisting of:

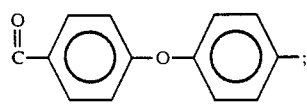

-continued

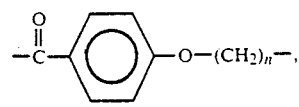

wherein n is an integer of from 1 to 10;

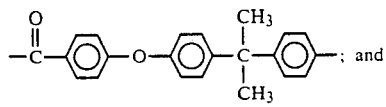

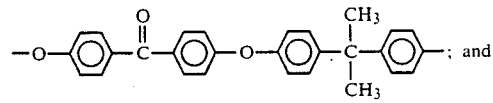

D is valence or a

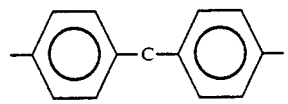

radical.

The novel bismaleimide compounds in accordance with this aspect of the present invention; may be prepared in accordance with known methods, such as by reacting maleic anhydride with an aromatic ether ketone diamine compound in the presence of acid and heating to a temperature above about 250° C.

The novel bismaleimides may be used as comononers, together with the epoxidic prepolymers, in curable epoxy resin formulations, such as those described above, or they may be homopolymerized and copolymerized in accordance with known free radical polymerization techniques.

Other preparation methods and end uses may suggest themselves to those skilled in this art, acquainted with the uses of bismaleimide compounds. Substituting the novel aromatic ether-ketone backbone as the amine moiety in the bismaleimide in accordance with the present invention may generally provide improved impact resistance and moisture resistance properties over earlier bismaleimides derived from aromatic diamines, ether-sulfone diamines or simpler ether ketone diamines.

In another aspect, the novel aromatic ether ketone diamine compounds of the present invention are useful as comonomer reactants for making new and improved polyamide resins and compositions.

More particularly, new and improved polyamides may be prepared in accordance with the present invention under condensation polymerization conditions by reacting a dicarboxylic acid or mixture of such acids with a novel aromatic ether-ketone diamine of the present invention or mixtures of these novel diamines, or mixtures of one or more of the novel diamines with other known diamines, such as hexamethylenediamine or diaminodiphenyl methane, under a nitrogen blanket, with or without a vacuum in the presence of condensation catalyst.

Suitable dicarboxylic acids include both aliphatic and aromatic dicarboxylic acids known to those skilled in this art. Illustrative aliphatic acids include, for example, saturated and unsaturated aliphatic dicarboxylic acids such as malonic, succinic, glutaric, adipic, maleic, fumaric and the like. Illustrative aromatic dicarboxylic acids include, for example, phthalic acid, isophthalic acid, and terephthalic acid, to name but a few. In addition, reactive derivatives of these dicarboxylic acids such as acid chlorides may also be employed.

Any of the known condensation catalysts may be employed such as for example, alkali or alkaline earth metal oxides, carbonates, and alcoholates, antimony compounds, tin compounds and the like.

The new and improved polyamide compounds in accordance with the present invention will generally comprise polyamides having repeating units of the formula:

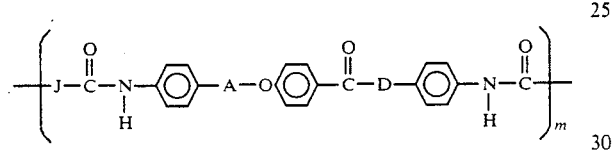

wherein m is an integer of from about 5 to about 250; J is a divalent, aliphatic cycloaliphatic, aromatic or aralkyl radical, A is a valence bond or a divalent radical selected from the group consisting of:

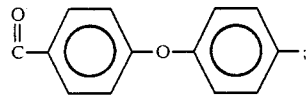

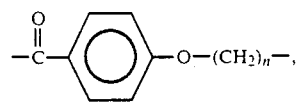

wherein n is a integer of from 1 to 10;

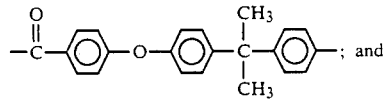

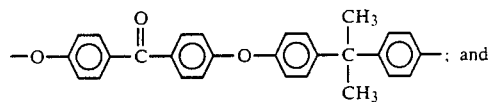

D is valence bond or a

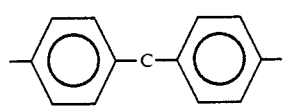

radical.

The new and improved polyamide compounds of the present invention generally exhibit improved impact strength, solvent resistance and moisture resistance over conventional polyamide resins, such as Nylon 6.

In still another preferred embodiment of the present invention the novel aromatic ether-ketone diamine compounds are useful as starting materials for making new and improved high temperature heat resistant polymeric materials.

In accordance with this embodiment of the present invention, novel polyimide compounds are provided in the form of compounds comprising repeating units of the formula:

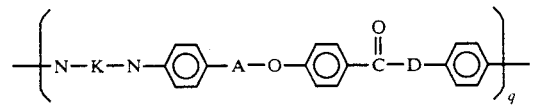

wherein q is an integer of from about 5 to about 250; k is a dianhydride compound selected from the group consisting of:

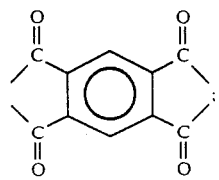

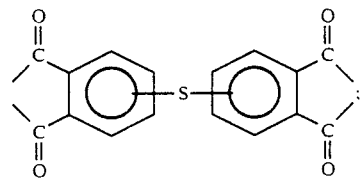

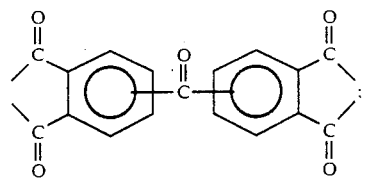

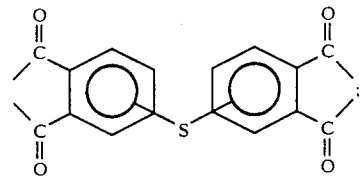

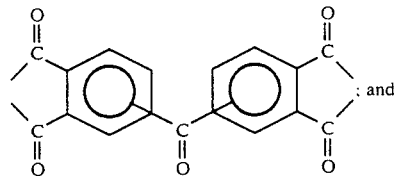

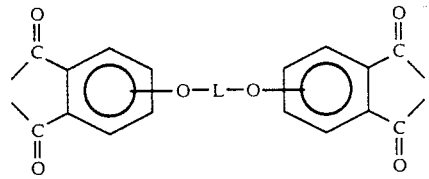

wherein L is selected from

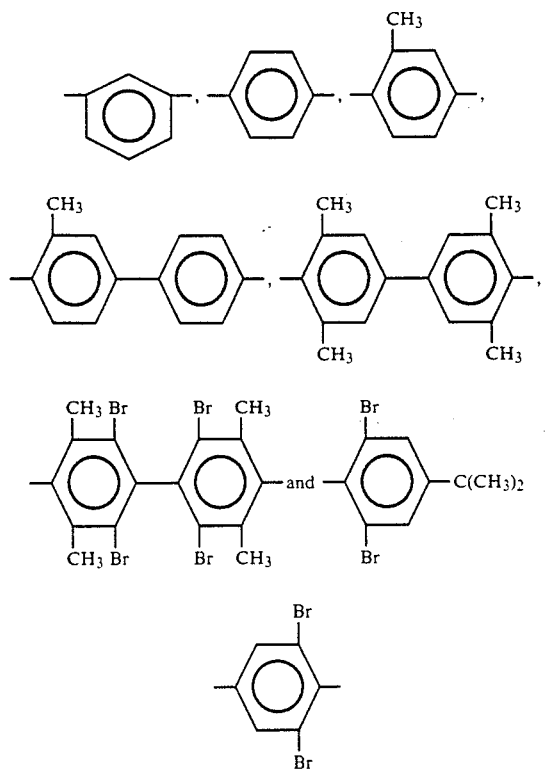

and divalent organic radicals of the general formula

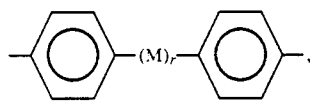

where M is a member selected from the class consisting of divalent radicals of the formulas, —$C_5H_2$—,

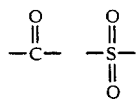

—O— and —S— where O is 0 or 1, S is a whole number from 1 to 5, the divalent bonds of the —O—L—O— radical are situated on the phthalic anhydride end groups, e.g., in the 3,3', 3,4'-4,3'- or the 4'4'-positions; wherein A is a valence bond or a divalent radical selected from the group consisting of:

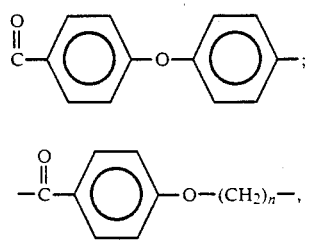

wherein n is an integer of from 1 to 10;

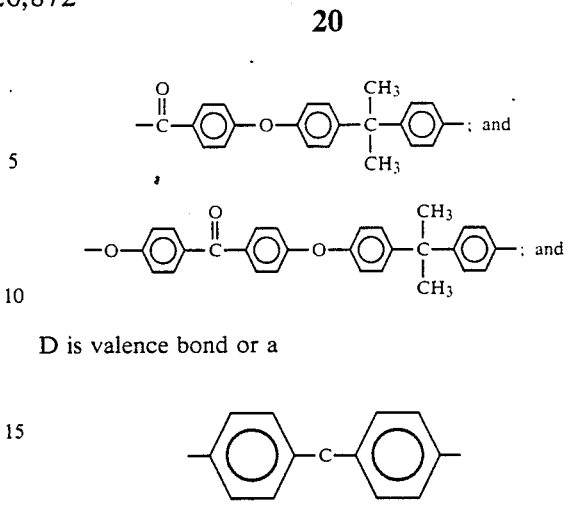

D is valence bond or a

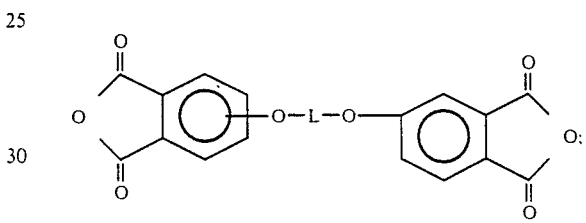

radical.

The new and improved polyimide compounds in accordance with the present invention may be generally prepared by reacting at least one dianhydride compound of the formula:

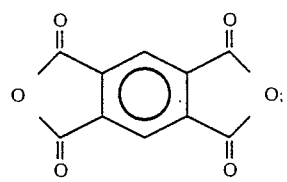

wherein L is the same as defined above; or pyromellitic dianhydride of the formula:

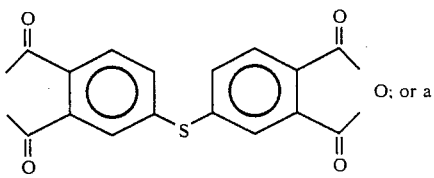

or a sulfur dianhydride of the formula:

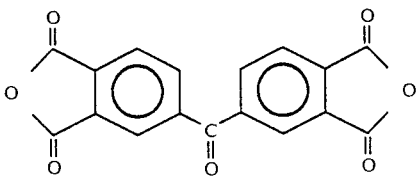

benzophenone dianhydride of the formula:

or mixtures thereof with a novel aromatic ether-ketone diamine compounds of the present invention alone, or in admixture with other diamine compounds. Reaction can be advantageously carried out employing well known solvents, such as o-dichlorobenzene, m-cresol/toluene, etc., in which to effect interaction between the dianhydrides and the novel ether-ketone diamines, at temperatures of from about 100° to about 250° C. Alternatively, the polyetherimides may be prepared by melt polymerization where the dianhydrides are reacted with the novel ether ketone diamines while heating the mixture of ingredients at elevated temperatures with concurrent intermixing.

Generally, melt polymerization temperatures of between about 200° to 400 ° C. and preferably 230° to 300° C. can be employed. Any order of additive of chain stoppers ordinarily employed in melt polymerization can be employed. The conditions of the reaction and the proportions of ingredients can be varied widely depending on the desired molecular weight, intrinsic viscosity and solvent resistance. In general, equimolar amounts of diamine and dianhydride are employed for high molecular weight polyetherimides, however, in certain instances, a slight molar excess (about 1 to 5 mol percent) of diamine can be employed resulting in the production of polyetherimides having terminal amine groups. The polyetherimides are injection moldable and can be reinforced by fillers, such as silica, carbon, fibers, glass fibers, etc., in which the filler comprises on a weight basis from 20 to 200 parts of filler per 100 parts of polymer.

The polyimide resins of the present invention exhibit excellent high temperature resistance and also exhibit improved impact resistance, solvent resistance and moisture resistance. They are extremely well-suited for use in high temperature and electrical applications, such as for cable jacketing and in wire enamels applications.

Another new and improved high temperature resistant polymer in accordance with the present invention comprises a copolymer comprising units of the formula:

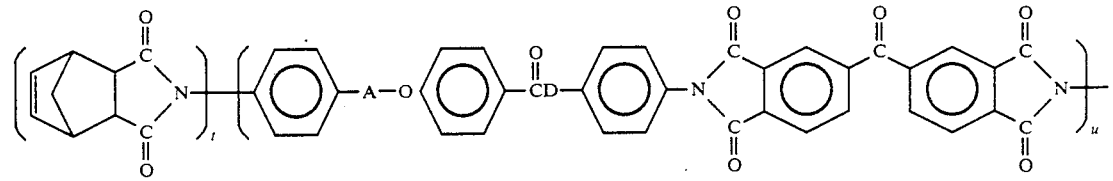

wherein t is 0-2 and u is 5 to 250, wherein A and D are the same as defined above, throughout this specification. The novel copolymer defined above may be prepared by polymerizing one or more of the novel ether-ketone diamine compounds of the present invention with a polymerizable monomer reaction mixture comprising nadic anhydride and a di or triester of benzophenone tetracarboxylic acid or benozphenone tetracarboxylic acid anhydride, with or without a conventional solvent, at elevated temperatures of from about 200° to about 400° C.

In order that those skilled in this art may better understand how the present invention may be practiced, the following examples are provided by way of illustration and not by way of limitation.

PREPARATION 1

Synthesis of 3-Nitro-4'-Chlorobenzophenone

A mixture of m-nitrobenzoyl chloride 23.25 g (0.12 mol), chlorobenzene 25 ml (0.25 mol) and anhydrous aluminum chloride 17.5 g (0.13 mol) was stirred at 80°-100° C. for 4 hrs. After cooling, the reaction mixture was poured into ice-water with rapid stirring. The white precipitate obtained was collected by filtration and washed with water and then hexane. The white solid was recrystallized from hexane/$CH_2Cl_2$ to provide a solid with a melting point of 95°-96° C.; yield 76%.

PREPARATION 2

Synthesis of 4-Nitro-4'-Chlorobenzophenone

The procedure of Preparation 1 was repeated exactly with the exception that instead of m-nitrobenzoyl chloride, p-nitrobenzoyl chloride was used as the starting material. 4-nitro-4'-chlorobenzophenone product having a melting point of 97°-98° C. was obtained in 79% yield.

PREPARATION 3

Reduction of 3-Nitro-4'-Chlorobenzophenone to 3-Amino-4'-Chlorobenzophenone

To a solution of stannous chloride dihydrate 19 g (0.074 mol) in 20 ml of concentrated hydrochloric acid, 4-nitro-4'-chlorobenzophenone of Preparation 1, 5 g (0.019 mol) was added in small portions, while reaction was being heated on a hot plate (reaction temperature 60°-100° C.). After the addition was complete, the reaction mixture was further stirred at 95° C. for 2 hours. The reaction mixture was cooled to room temperature and then poured slowly into 100 ml of 40% sodium hydroxide solution. Ice was added during neutralization to maintain the temperature below 10° C. The precipitate was collected by filtration and washed with water until free of alkali. After drying, the yellow solid was recrystallized from ethanol to provide 3.76 g (86) of 3-amino-4'-chlorobenzophenone m.p. 114°-115° C., NMR ($COCl_3$)δ3.8 (broad S, 2H, $NH_2$), 6.55-7.63 (Ar-H 8-H).

Analysis by high resolution mass spectrometry confirmed the product to be $C_{13}H_{10}NOCl$, mw 231.0449.

PREPARATION 4

Reduction of 4-Nitro-4'-Chlorobenzophenone to 4-Amino-4'-Chlorobenzophenone

The procedure of Preparation 3 was followed exactly using the 4-nitro-4'-chlorobenzophenone product of Preparation 2 as the starting material. After drying, the product was recrystallized from ethanol to 93% yield of product having m.p. 178°-180° C.; NMR (DMSO-$d_6$)δ6.13 (S, $NH_2$, 2H), 6.57 (d, 3.5 Ar-H, J=9Hz, 2H), 7.48 (d, 3.5-Ar-H, J=8Hz, 2-H, J=8Hz, 2H); 7.54 (S, 2.6-Ar-H, 2',6'-Ar-H, 4H). Mass specturm analyzed for $C_{10}H_{13}NOCl$, MW (231.0489).

EXAMPLE 1

Synthesis of 3-Amino-4'-(M-Aminophenoxy) Benzophenone

A solution of m-aminophenol 25 g (0.23 mol.) in 160 ml of dimethylsulfoxide and 190 ml of toluene was degassed for 30 minutes by bubbling nitrogen. The temperature was raised to 50° C. and 9.16 g (0.23 mol) of sodium hydroxide as 50% aqueous solution was added. The reaction temperature was slowly raised to 110° C. (oil bath 140° C.) and water was distilled off via toluene-water azeotrope. After all the water was distilled off, the toluene was distilled off till the reaction temperature reached 160° C. Reaction mixture was cooled to 80° C. and 3-amino-4'-chlorobenzophenone 53 g (0.23 mol) was added in small portions. After the addition was complete the reaction temperature was raised to 150° C. and maintained for 4 hours. After cooling to room temperature, the reaction mixture was poured into 800 ml of 2% sodium hydroxide and 1% sodium sulfite solution with rapid stirring. The precipitate semi-solid obtained was washed with water and then taken up in 200 ml of chloroform. The chloroform solution was washed twice with water. After drying with magnesium sulfate, chloroform was removed to provide a dark yellow resin like solid 52.3 g (72%), m.p. 48°–52° C.

PREPARATION 5

Synthesis of 4,4'-bis(m-aminophenoxy) benzophenone.

4,4'-bis(m-aminophenoxy)benzophenone was prepared in accordance with the method of Example 1 employing 4,4'-dichlorobenzophenone and m-aminophenol as the starting materials. 26% yield of product having a melting point of about 138°–140° C. was obtained.

PREPARATION 6

Synthesis of 4,4'-Bis(p-Aminophenoxy)benzophenone
4,4'-bis(p-aminophenoxy)benzophenone was prepared in accordance with the method of Example 1 employing 4,4'-dichlorobenzophenone and p-aminophenol as the starting materials. 51% yield of a product having a melting point of about 150°–152° C. was obtained.

EXAMPLE 4

Synthesis of 1,4-Bis(3-Aminobenzophenoneoxy)benzene 1,4-bis(3-aminobenzophenone-oxy)benzene was prepared in accordance with the method of Example 1 using 3-amino-4'-chlorobenzophenone and hydroquinone starting materials, good yield of a product having a melting point of about 130°–135° C. was obtained.

EXAMPLE 5

Synthesis of 1,4-Bis(3-Aminobenzophenone-4-Oxyphenyl)propane 2,2,-bis (3-aminobenzophenone-4-oxyphenyl) propane was prepared in accordance with Example 1, using 3'-amino-4'-chlorobenzophenone and bisphenol-A as the starting materials. Good yields of the product having a melting point of about 85°–90° C. was obtained.

EXAMPLE 6

Synthesis of Long Chain Ester Ketone Diamine

A long chain ester ketone diamine was prepared by reacting m-aminophenol 20.75 g (0.19 mol), bisphenol-A, 21.49 g (0.09425 mol), 4,4'-dichlorobenzophenone 47.36 g (0.1886 mol) in a solution of NaOH 15.12 g (0.378 mol) as 50% solution, dimethylsulfoxide 110 mls, toluene 110 mls in accordance with the procedure of Example 1. 93% yield of a product having a melting point of about 80°–90° C. was obtained. This synthesis may be summarized by the following equation:

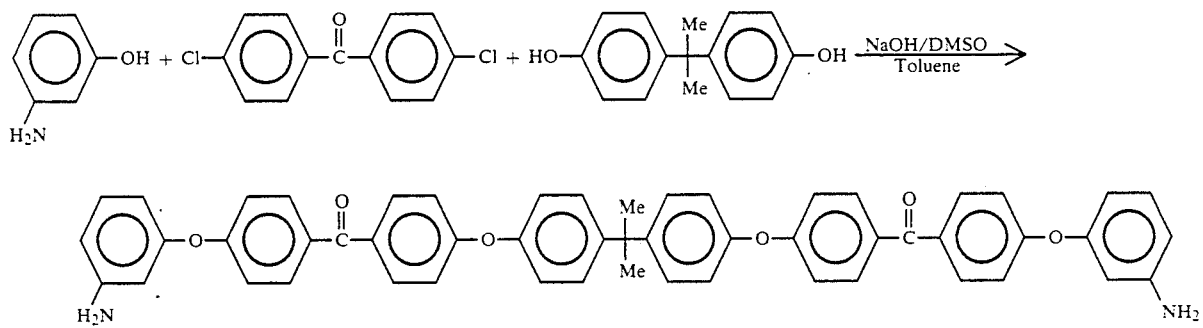

PREPARATION 7

It was attempted to synthesize a flexible ether ketone diamine having the formula:

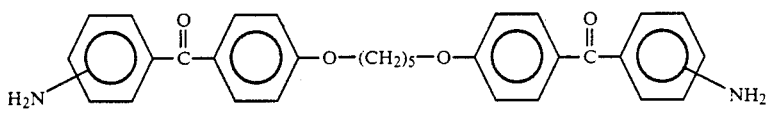

in accordance with the method of Example 1 using 3-amino-4'-chlorobenzophenone and 1,5-pentanediol as starting materials with the exception that the reaction medium was comprised of sodium hydride in tetrahydrofuran, instead of NaOH in DMSO.

Analysis of the reaction product by NMR showed the absence of downfield doublets and the IR showed the absence of a carbonyl group.

Both the NMR and IR spectra obtained were found to be consistent with a product having the structure:

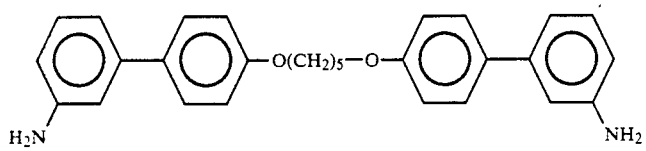

a compound having a melting point of about 89°-91°. The product obtained resulted from decarbonylation of the substituted benzophenones.

EXAMPLE 7

Synthesis of Flexible Ether Ketone Diamine

A flexible ether ketone diamine having the formula:

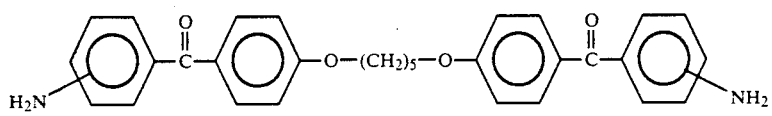

was prepared as follows:

1,5-diphenoxypentane and m-nitrobenzoyl chloride were reacted in the presence of aluminum chloride catalyst to form:

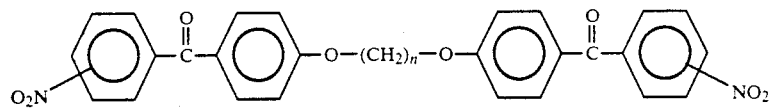

This intermediate product was then reduced with stannous chloride and hydrogen chloride in accordance with the method of Preparation 3 to yield the flexible ether ketone diamine product.

EXAMPLES 8-13

The novel ether-ketone diamines of the present invention provide improved epoxy resin compositions.

The following procedure was used to prepare and cure neat resin compositions: the epoxide prepolymer and the polyamine component were mixed at 125° C. for 5 minutes, and cooled to 100° C., the catalyst, if any, was mixed in, and the mixture was degassed for 10 minutes. The liquid resin was then poured into a mold and cured for 2 hours at 135° C. and for 3 hours at 177° C. Properties were determined by the following procedures. The flexural test is described in ASTM D-790, Method I. Dynamic Mechanical Analyzer, and Tg was defined as the temperature at which the loss tangent, tan δ, is a maximum. ASTM D4065 test method covers this type of Tg measurement. Conditioning before testing is described by the phrases "wet" and "dry". "Wet" refers to conditioning by immersion of the sample in distilled water for the times and temperatures stated, prior to testing at 93° C.

The compressive strength was measured on a modified ASTM D695 specimen, described in D. H. Woolsencraft et al, COMPOSITES, Oct. 1981, pages 275-280. The prior art diamines, both them simple ether-ketone diamines, described in copending application Ser. No. 584,700, filed Feb. 29, 1984, now U.S. Pat. No. 4,645,803 were tested for comparison.

The epoxy resin formulations prepared and the results obtained are set forth in Table 1 as follows:

TABLE 1

FLEXURAL PROPERTIES OF ETHER KETONE DIAMINE CURED EPOXY RESIN COMPOSITIONS

| COMPOSITION (pbw) | A* | B* | 8 | 9 | 10 | 11 |
|---|---|---|---|---|---|---|
| N,N,N',N'-tetraglycidyl 4,4'-diaminodiphenylmethane[a] | 1.0 | 1.0 | 1.0 | 1.0 | 1.0 | 1.0 |
| [b structure] | 0.75 | — | — | — | — | — |
| [c structure] | — | 0.75 | — | — | — | — |
| [d structure] | — | — | 0.75 | — | — | — |

TABLE 1-continued
FLEXURAL PROPERTIES OF ETHER KETONE DIAMINE CURED EPOXY RESIN COMPOSITIONS

| | structure e | | | 0.75 | | |
| | structure f | | | | 0.75 | |
| | structure g | | | | | 0.75 |

| PROPERTIES | A* | B* | 1 | 2 | 3 | 4 |
|---|---|---|---|---|---|---|
| Tg, °C. | 250 | 225 | 240/ | 179 | 215 | 217 |
| Modulus (MSI) | | | | | | |
| dry | 0.567 ± 0.007 | 0.501 ± 0.035 | 0.620 ± 0.005 | 0.596 ± 0.004 | 0.623 ± 0.004 | 0.575 ± 0.003 |
| wet[1] | 0.434 ± 0.018 | 0.399 ± 0.004 | 0.498 ± 0.078 | 0.493 ± 0.012 | 0.453 ± 0.010 | 0.451 ± 0.008 |
| Strength (KSI) dry | 18.4 ± 1.2 | 15.7 ± 1.4 | 17.8 ± 0.9 | 17.7 ± 0.8 | 21.3 ± 0.6 | 19.1 ± 0.9 |
| Failure Strain, % dry | 3.41 ± 0.23 | 3.33 ± 0.31 | 2.93 ± 0.15 | 2.99 ± 0.14 | 3.56 ± 0.13 | 3.48 ± 0.24 |
| Work to break, in-lbs/in.[3] dry | 344 ± 45 | 280 ± 53 | 260 ± 28 | 287 ± 25 | 415 ± 28 | 357 ± 46 |

*Prior art Composition.
[a]ARALDITE ® MY 720, Ciba-Geigy Corporation
[b]See Ser. No. 584,700, filed February 29, 1984 and Preparation 5.
[c]See Ser. No. 584,700, filed February 29, 1984 and Preparation 6.
[d]See Example 1
[e]See Example 4
[f]See Example 5.
[g]See Example 6.
[1]immersed in distilled water for 14 days at 93° C.

All the castings were cured at 135° C. for 2 hours and 180° C. for 3 hours. This procedure provided void free 5×5 in, 1/16 thick plaques.

The flexural testing data are summarized in Table I. All these resin systems except for the diamine of comparative Example B show good dry modulus and excellent retention of modulus under hot/wet conditions. The wet moduli obtained with Example 8 and Example 11 are among the highest we have observed with any other diamine cured epoxy system.

The flexural properties seem to be independent of the chain length of the diamines. All these systems show strain to failure and the strength values similar or higher than the same epoxy resin cured with diaminodiphenyl sulfone. The glass transition temperature however does show a decrease with the increase in chain length. This may be due to increase in crosslink density as the chain length increases.

Of all the ether-ketone diamines, the hydroquinone derived diamine of Example 9 provides the best overall properties.

Each of the above-mentioned patents, applications and publications are specifically incorporated herein by reference. Although the present invention has been described with reference to certain preferred embodiments, it is apparent that modifications or changes may be made therein by those skilled in this art, without departing from the scope and spirit of the present invention, as defined by the appended claims.

What is claimed is:
1. A compound of the formula:

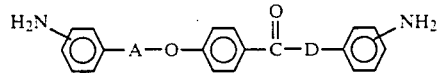

wherein A is valence bond or a divalent radical selected from the group consisting of:

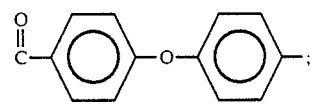

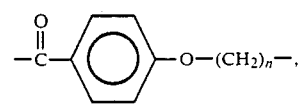

wherein A is a valence bond or a divalent radical selected from the group consisting of:

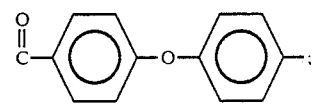

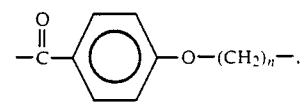

wherein n is an integer of from 1 to 10;

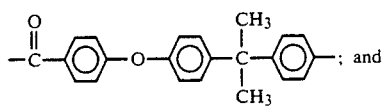; and

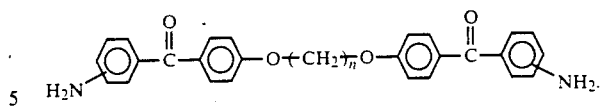

5. A diamine compound of the formula:

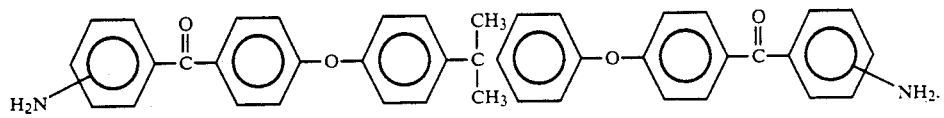

6. A diamine compound of the formula:

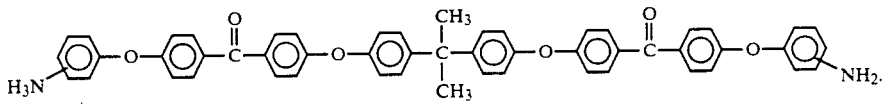

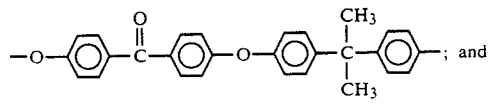; and

D is valence bond or a

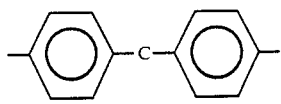

radical.

2. A diamine of the formula:

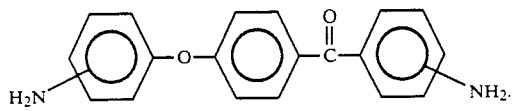

3. A diamine compound of the formula:

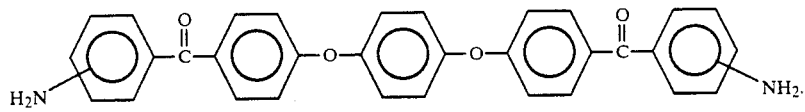

4. A diamine compound of the formula:

7. A method for the preparation of an aromatic ether-ketone diamine compound, said method comprising:
  (a) forming a reaction mixture comprising: 3- or 4-amino-4'-chlorobenzophenone and
    (i) m- or p- aminophenol;
    (ii) a dihydric phenol compound; or
    (iii) mixtures of (i) and (ii) in an alkaline medium in a polar aprotic; and
  (b) reacting the components of reaction mixture (a) at a temperature of between about 30° C. and 300° C. until the reaction is substantially complete.

8. A method for the preparation of an aromatic ether-ketone diamine compound, said method comprising:
  (a) forming a reaction mixture of
    (i) 3- or 4-amino-4'-chlorobenzophenone and
    (ii) a disodium salt of a dihydric phenol or a sodium salt of m- or p- aminophenol, in dimethyl sulfoxide; and
  (b) reacting the reaction mixture of step (a) at a temperature of between 30° C. and 300° C. until the reaction is substantially complete.

* * * * *